(12) United States Patent
Salem et al.

(10) Patent No.: US 6,222,524 B1
(45) Date of Patent: *Apr. 24, 2001

(54) MOUTH OPERATED INPUT DEVICE FOR AN ELECTRONICALLY RESPONSIVE DEVICE

(75) Inventors: Christopher Jesse Salem, Cupertino; Shumin Zhai, San Jose, both of CA (US)

(73) Assignee: International Business Machines Corporation, Armonk, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/917,393

(22) Filed: Aug. 25, 1997

(51) Int. Cl.[7] .................................................. G09G 5/08
(52) U.S. Cl. ...................................... 345/157; 340/825.19
(58) Field of Search .................................. 345/157, 156, 345/158; 341/21; 340/825.19

(56) References Cited

U.S. PATENT DOCUMENTS

| | | | |
|---|---|---|---|
| 4,680,577 | * 7/1987 | Straayeret et al. | 340/711 |
| 4,783,656 | * 11/1988 | Katz et al. | 340/825.19 |
| 4,817,950 | * 4/1989 | Goo | 273/148 B |
| 5,489,900 | 2/1996 | Cali et al. | |
| 5,521,596 | 5/1996 | Selker et al. | |
| 5,579,003 | 11/1996 | Rutledge et al. | |
| 5,694,152 | * 12/1997 | Loop | 345/157 |
| 5,812,114 | * 9/1998 | Loop | 345/157 |

FOREIGN PATENT DOCUMENTS

2259970 * 3/1993 (GB) .

* cited by examiner

Primary Examiner—Bipin Shalwala
Assistant Examiner—Vanel Frenel
(74) Attorney, Agent, or Firm—Merchant, Gould, Smith, Edell, Welter & Schmidt; Altera Law Group, LLC

(57) ABSTRACT

A mouth mounted pointing device for use with an element to be moved on a computer. A control element having a surface for tongue interaction causes the control element to interact with a transducer responsive element to operate an electronic circuit, which moves the computer element. A second control element operates a switch for the circuit.

9 Claims, 3 Drawing Sheets

MOUTH OPERATED INPUT DEVICE FOR AN ELECTRONICALLY RESPONSIVE DEVICE

BACKGROUND OF THE INVENTION

1. Field of the Invention

This invention relates to an electronic input device for operating an electronic system. In particular, it concerns an input device for operating a cursor in a computer system. More particularly, the invention is directed to a pointing device operated by the tongue of a user.

2. Description of Related Art

The success of the modern WIMP (Windows, Icons, Menus and Pointers) interfaces have made pointing or input devices, such as the mouse, the trackball, and in keyboard isometric joysticks, e.g., the Trackpoint®, an essential part of computer systems. Patents that relate to the Trackpoint® pointing device are U.S. Pat. Nos. 5,489,900; 5,579,033; and 5,521,596. The disclosure thereof are incorporated by reference herein.

The majority of the current input devices are designed for hand use. Due to various physical disabilities, however, there is an unfortunate population of users who are unable to use hand operated input devices and methods. The use of hand pointing input devices are also problematic for restrictive environments and tasks that need both hands to be completely dedicated to a specific operation other than using the pointing device. Such tasks might include driving, piloting, or underwater exploration. As a result, alternative input devices, such as the mouse, the trackball, head mounted pointers, chin mounted joysticks, eye tracking, and voice recognition have all been developed for interaction with WIMP interfaces. Although all of these alternative input devices are somewhat successful, they are also limited in many aspects.

There is accordingly a need to provide a pointing or input device for operating an electronic system such as a computer which is ergonomically and finctionally more satisfactory than known systems.

This invention is directed to providing a pointing or input device which minimizes the disadvantages of other known systems.

SUMMARY OF THE INVENTION

By this invention there is provided a system which reduces the disadvantages of the known pointing and steering devices.

This invention is directed to using the mouth, and particularly, the tongue of a user to operate a device, such as a pointing device for a computer.

According to the invention, there is provided a pointing, input, and/or steering device for use with a computer, and other electronic devices. When used with a computer the pointing device is conventionally known as an input device.

In a preferred form of the invention, the input device for the computer is tongue operated. Thus, the invention includes means to affect positioning of a cursor on a computer screen and to affect clicking and dragging as is required in the common computer environments by use of mouth interaction, and particularly tongue interaction, with the device.

The isometric pointing device comprises a first control element to interact with a transducer responsive element to operate the electronic circuit and thereby move an element, such as a cursor, on a computer. The first control element includes a stick for tongue interaction to cause the control element to move and thereby operate the electronic circuit.

A dental appliance, namely a mouthpiece, is fitted at least partially in the mouth for mounting the first control element, which includes the stick, for projection into the mouth cavity, into the area or space above the normal position of repose of the tongue.

There are means whereby the electronic circuit provides an output signal in response to the condition of the transducer responsive element, and there are means for transmitting the output signal to the computer and thereby move an element, such as a cursor, on the computer.

The device may include an electronic circuit and one or more switches responsive to pressure thereby to selectively open and/or close the electronic circuit.

An article by S. Zhai, P. Milgram, and W. Buxton, "The Influence of Muscle Groups on Performance of Multiple Degree-of-Freedom Input," *Proc. of CHI'96: Human Factors in Computing Systems* (1996), pp. 308–321, shows the somatosensory and motor cortex homunculi, and also shows that the tongue and the mouth occupy an amount of sensory and motor cortex that rivals that of the fingers and the hand. Furthermore, unlike the eyes, which have rich cortex representation but are not manipulation organs, the mouth and the tongue are evolved for manipulation. Although not naturally used for pointing, the tongue constantly performs sophisticated motor control for vocalization and mastication. This provides the significant potential of using the tongue and the mouth for computer input.

The invention is further described with reference to the accompanying drawings.

BRIEF DESCRIPTION OF THE DRAWINGS

The present invention, both as to its organization and manner of operation, together with further objects and advantages thereof, may best be understood with reference to the following description, taken in connection with the accompanying drawings in which.

DETAILED DESCRIPTION OF THE PREFERRED EMBODIMENT

Figure 1:
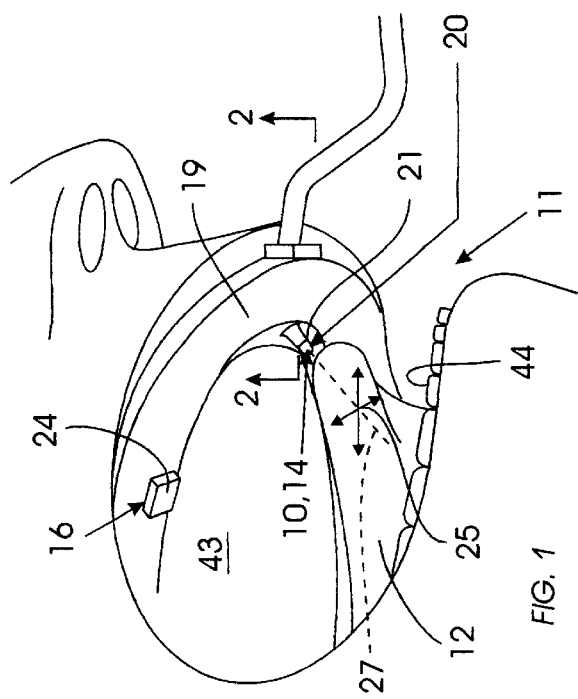
FIG. 1 is a perspective view from underneath showing a mouth, teeth, and tongue together with the mouth operated pointing device, namely an input device, for use with a computer.

FIG. 1 shows a pointing and/or steering device 10 in the form of an input device to be operated in the mouth 11, namely by a tongue 12 of an operator. The pointing device 10 is provided for use with a computer 13 and other electronic devices.

When used with a computer 13 the pointing device 10 is an input device. The pointing device 10 for the computer 13 is mouth operated, such that a tongue 12 can effectively move in different directions to control the pointing device 10.

Figure 5:
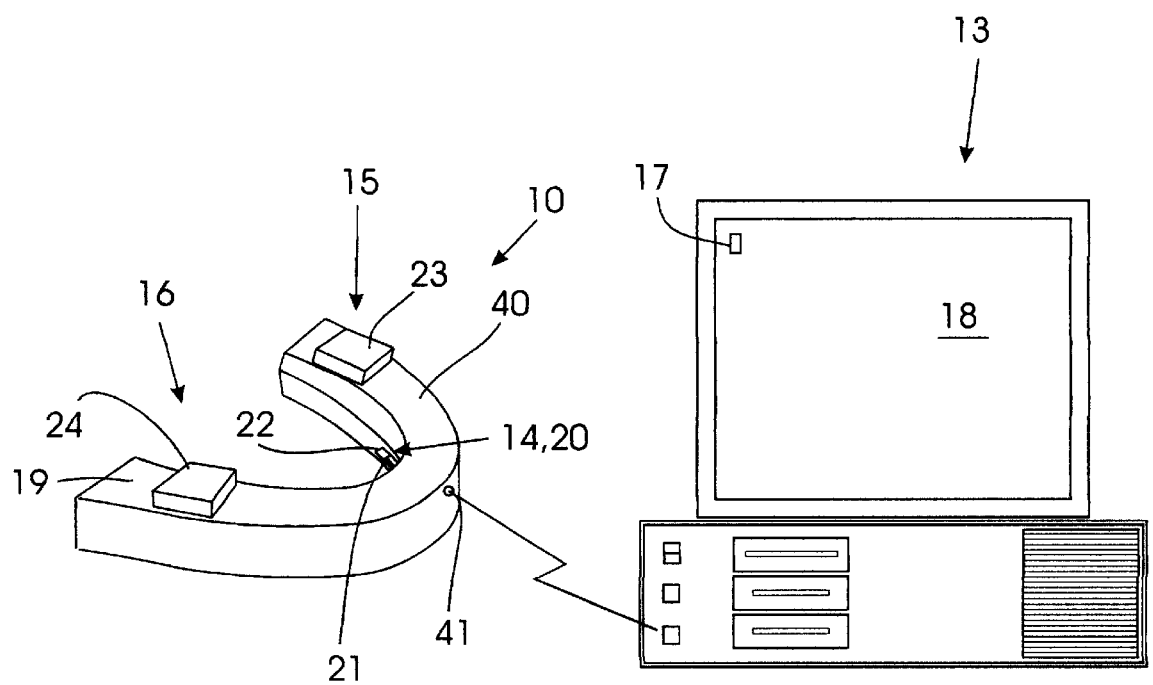
FIG. 5 is a view of a tongue pointing device having a first control element, a second control element, and a third control element connected to a computer.

There is a first control element 14, second control element 15, and third control element 16 to affect pointing of a cursor 17 on a computer monitor screen 18 as shown in FIG. 5. This permits clicking and dragging, as is required in the common computer environments, by use of tongue interaction with the device. As described, the pointing or steering device 10 would operate the cursor 17 on the computer screen 18. The second and third control elements 15 and 16, respectively, would be for clicking, and dragging a cursor 17 on the computer screen 18 as required. The location of the second control element 15 and third control element 16 can be adjacent to the first control element 14 and also be mouth operated.

Since the tongue 12 has a limited range of movement, an isometric first control element 14 of the pointing device 10 is useful. Unlike the fingers which can extend and reach, the tongue 12 mostly stays inside of the mouth 11 where space is limited. The pointing device 10 is designed to take advantage of the limited range of movement of the tongue 12. Because pressure sensitive isometric joysticks can be small and do not require a large range of motion they are suitable for mouth 11 operation to perform cursor 17 control.

The tongue operated isometric input device 10 of the invention uses the IBM Trackpoint III®. The tongue operated isometric input device 10 includes a mouthpiece 19 that is similar to a dental night guard or a sports mouth guard. It is form fitted to each individual's upper teeth 42 and hard pallet 43. Because of the custom fit of the mouthpiece 19, the user may relax at normal jaw posture when wearing the mouthpiece 19. Speaking with the device 10 inserted in the mouth is also feasible. The mouthpiece 19 is constructed of soft form fitting plastic that can be custom fitted to the individual user's mouth 11 in about 5 minutes. This provides a secure platform for the tongue 12 to manipulate the joystick.

The sports guard product becomes malleable by putting it in hot water, and this allows the mouthpiece 19 to conform to the mouth 11 and/or teeth 42 and 44 of the user. An advantage of this system is that it permits the use of the pointing device 10 with the jaw retained in a slack position.

In different cases the pointing device 10 may be provided separately to be fitted with the mouthpiece 19 after the mouthpiece 19 is set for the mouth of a particular user. Suitable calibration can then be worked out for the pointing device. In yet other forms the pointing device 10 and the mouthpiece 19 can be an integral unit.

Figure 2:
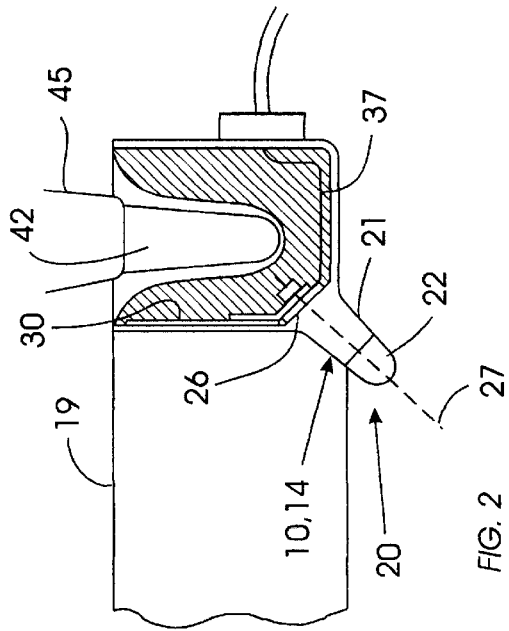
FIG. 2 is a view through line 2—2 of the tongue pointing device of FIG. 1, showing in further detail the components constituting the input device and the mouthpiece of the first control element.

As shown in FIG. 2, a Trackpoint® stick device 20 is mounted onto the mouthpiece 19, near the roots 45 of the front teeth 42. The shaft 21 of the Trackpoint® stick is about 1 cm long, and points downwards and inwards, towards the tongue tip. The shape of the shaft 21 is conical so as to facilitate a greater ability for the tongue 12 to manipulate the shaft 21 from all directions. The tip 22 of the joystick 20 is composed of a soft rubber to cushion the tongue 12 against the device. In other cases the stick would be shorter than about 1 cm, namely in the range of about 0.5 cm.

As seen in FIG. 5, each of the control members 15 and 16 controls one or more switches, which are designed for button selection. The second control 15 includes a modular bite switch which is attached anywhere between the upper and lower teeth 42 and 44 so as to allow for button selection by biting. A third control member 16 with another switch, and is shown inside the mouth. It could 10 alternatively be linked to the inside of the mouth or outside of the mouth. It can be provided so as to allow for button operations by any other body organ, for instance the hand or foot.

First Control Element and Transducer

Figure 4A:
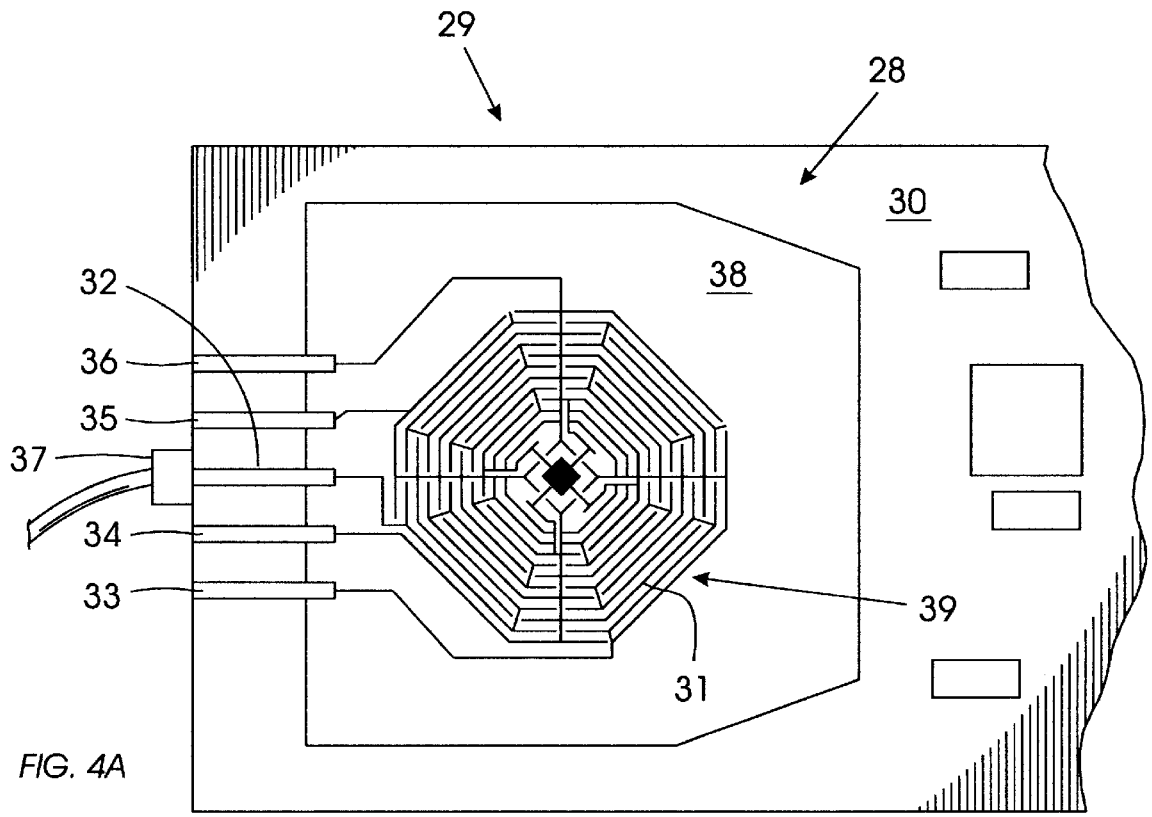
FIG. 4a is a view of strain gauges on a shaft having a strain sensitive or pressure transducer configuration for responding to the changes of position of the pointing stick.
Figure 4B:
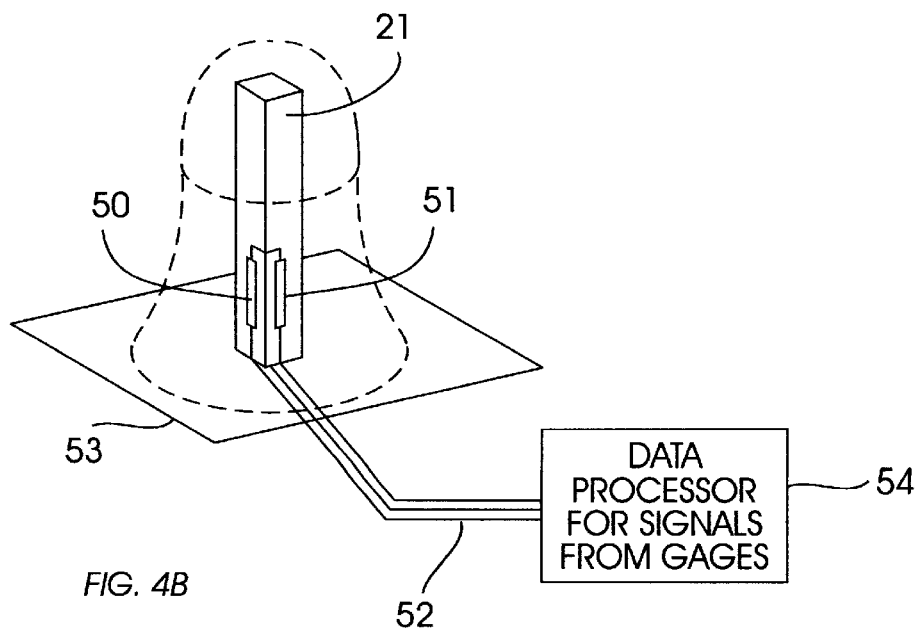
FIG. 4b is a view of an alternative transducer system, namely a flexible sheet having, for instance, a strain sensitive array, a pressure transducer array, or capacitive array for responding to the changes of position of the pointing stick.

Referring to FIGS. 2, 4a, and 4b, the first control element 14 for the device 10 includes the stick 21 for application of pressure. When pressure is applied to the stick 21 of the first control element 14 by the tongue 12, the first control element 14 is moved as indicated by arrow 25. The stick 21 can move as required about point 26 on axis 27. The stick 21 interacts with the transducer responsive element 28 to operate an electronic circuit and thereby move the cursor 17 of the computer 13.

The first control element 14 and the pressure responsive transducer element 28 interact whereby pressure applied to the pressure responsive element 28 can effect a relative electrical change of the electronic circuit on the board element 30. This acts to vary an output signal from the electronic circuit. In this manner applying pressure on a selected place and direction on the first control element 14 acts to change the condition of the transducer responsive element 28.

The transducer responsive element 28 is operated by the pointing stick 21 such that the angular movement controls the movement of the cursor 17 on the display screen 18. This stick 21 operates with ancillary means including the electronic circuit such that angular movement is converted to the movement of the cursor 17.

One form of transducer 28, namely a pressure transducer, for the electronic circuit operable with the first control element 14 is described. The transducer 28 operates as described with relation to FIGS. 4a and 4b. This is only an example form of a transducer that can be used to translate the action from the first control element 14 to an electric signal. There can be other forms of transducers 28 used to translate the action from the first control element 14 to an electrical signal, such as a strain sensitive array, a capacitive array, or other devices that translate motion into electrical signals.

In FIG. 4b, there are two strain gauges 50 and 51, with associated electrical leads 52. These are placed on orthogonal sides of a shaft 21. The shaft 21 is shown mounted on a plate 53. Strain gauges formed from piezoresistive sensors and other sensors are well known in the art. When the force is applied from the tongue 12 to the shaft 21, changes in voltage or resistance across the strain gauges are sensed. The resulting electrical signals reflect the direction and amount of force applied to the pointing stick 10. The generated signals are transmitted by leads 52 to a data processing unit 54 for processing the movement of the shaft 21. In the preferred embodiment, two strain gauges are used on two surfaces of the shaft at right angles. Under most operating conditions, two are adequate. Another alternative embodiment is to put four strain gauges on the shaft, one on each side of the shaft 21.

In FIG. 4a, there is an overlay conductive element arrangement 31 that has five different terminals labeled 32–36 connected to an output device 37. Underneath the overlay conductive elements 31 is a conductive plate 38, with a given resistance per unit square (e.g., 500 ohms/square mm).

The terminals 32–36 are respectively connected to different traces 39 on the conductive elements 31, all of which are conductive. As more of the conductive traces 39 touch the conductive plate 38, the resistance decreases. There is a larger current carrying area for the electrons as more conductive traces 39 touch the conductive plate 38.

Terminal 32 is the common trace. It has "fingers" that interleave with all of the other traces. Trace 32 completes the circuit for all other traces.

Trace 33 is the "Down" trace. Trace 34 is the "Left" trace. Trace 35 is the "Up" trace. Trace 36 is the "Right" trace.

As a user presses down on a face plate, the pressure forces contact between the trace 32, and one or more of the other four traces 33 to 36, and the conductive plate 38.

For example, two scenarios are explained on how the pressure transducer works. The first example is that the user wants the cursor 17 on the computer screen 18 of computer 13 to move straight up, or north, on the screen 18, and the second example is that the user wants the cursor 17 to move in a southerly direction on the screen 18.

EXAMPLE 1

Straight Up (North)

For the user to move the cursor 17 straight north, the user would naturally tilt and press the tongue 12 forward. This motion would cause contact between trace 35, trace 32, and the conductive plate 38 underneath the overlay 31.

When the user wants to move the cursor 17 faster, the user would naturally tilt and press the tongue 12 harder in the forward direction. This additional pressure causes additional contact between the longer fingers of traces 39 towards the outside of the hexagonal overlay 31, reducing the resistance at a faster rate and causing more current to flow. This faster rate of resistance reduction will increase the speed of the cursor movement on the screen 18.

EXAMPLE 2

Southerly Direction

For the user to move the cursor 17 in a southerly direction, the user would naturally tilt the tongue 12 backwards. The tongue 12 movement provides both the north-south control and the east-west control. This motion would cause the trace 32 to contact the trace 34, which moves the cursor 17 to the left, and also cause the trace 35 to contact the trace 33. This moves the cursor 17 down. As with Example 1, the harder the tongue presses in that direction, the larger the contact area between the traces 39 and the conductive plate 38, making the cursor 17 move faster.

Any other desired movement of the cursor 17 is a similar motion to the above two examples.

The electronic circuit 29 operates as follows: as the user applies pressure to one or more of the four quadrants, the trace 39 for that quadrant becomes connected to the common portion of the plate 38. As more pressure is applied, the resistance decreases, since there is more current carrying area when more pressure is applied, therefore reducing the overall resistance. Since the voltage is constant, the current must increase to compensate for this change in resistance.

As the current changes, the resistors, capacitors, and driver for the output 38 change the intensity of the signal from the output 38. The circuit 29 can also perform the transformation from current into an increase in pulse repetition frequency (PRF), or from current into a different coding scheme to indicate a faster movement of the cursor 17.

Second Control Element

A second control element 15 is also mounted with the mouthpiece 19 and is responsive to mouth pressure, preferably pressure between the teeth 42 of the upper jaw and the teeth 44 of the lower jaw. Pressure is applied to the second control element 15 to cause the element to operate a switch 23. The second control element 15 is movable with respect to a mounting such that mouth action, particularly closure and opening of the teeth, acts to cause the second control element 15 to interact with the switch. The second control element 15 is located substantially removed from the first control element 14.

Both of the first and second control elements 14 and 15 are located in the top face 40 of a mouthpiece 19. The second control element 15 is located in a position of the mouthpiece 19 to act as an input device movable under pressure. This movement acts to operate the switch 23 for the electronic circuit 29. The switch is a mechanical element for the circuit 29.

The mounting is provided for the second control element 15 such that as teeth 44 engage with the second control element 15, that mouth action acts to cause the control element 15 to move and thereby interact with the switch.

Third Control Element

There is a third control element 16 located in a spaced location from the first and second control elements 14 and 15. The third control element 16 is also selectively operational by the teeth on the opposite side of the jaw or by the tongue. The third control element 16 is movable in relation to the mouthpiece 19.

There is a second switch 24 for the electronic circuit 29. This second switch 24 is operable under interaction from the third control element 16 to generate switching signals in the electronic circuit 29.

User Testing

An article by C. Salem, S. Zhai, entitled "An Isometric Tongue Pointing Device," *Proc. of CH'97: Human Factors in Computing Systems* (1997), pp.538–539, reports on two subjects who have conducted user testing. Neither subject had previous experience with an isometric pointing device. A custom fitting tongue device was made for each of the subjects. Each subject tested both a standard finger operated Trackpoint III® and the custom made tongue device. Subject 1 tested the tongue device first and the finger device later after a short break. Subject 2 had a reversed order.

The testing task was for the subject to select a highlighted button among an array of five by four buttons as quickly as possible. A beep was presented if the subject clicked outside of the range. The first 5 selections of each set were discarded as practice runs.

Figure 3A:
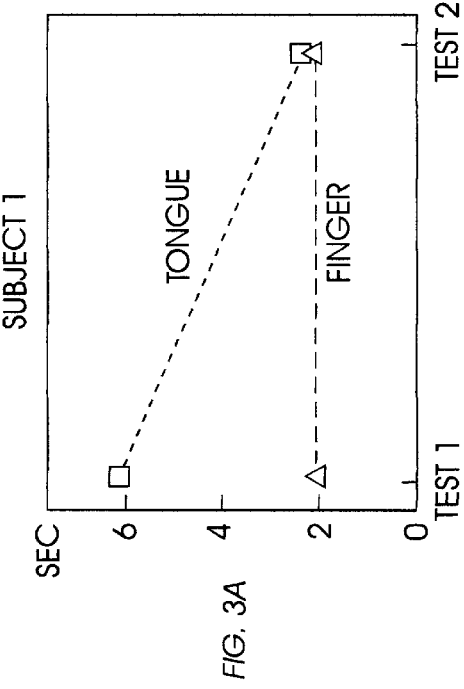
FIGS. 3a and 3b are graphical representations of the mean selection times showing the effectiveness of use of the invented system in comparison to using the conventional finger pointing device.
Figure 3B:
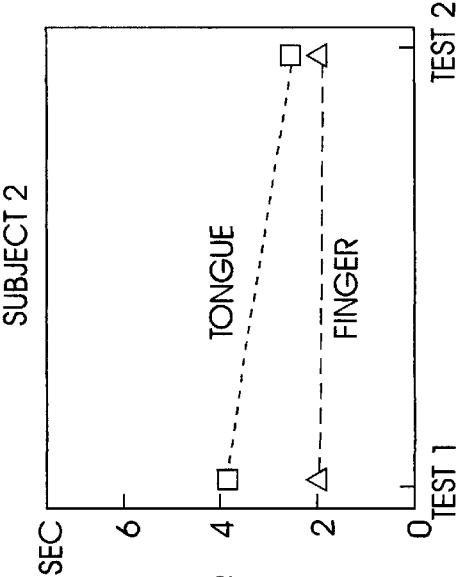

FIGS. 3a and 3b respectively show the mean selection time of Subject 1 and Subject 2 with both devices in each of the two tests. As can be seen, on average, the tongue device performed much poorer than the finger device in the beginning, probably due the fact that the tongue is not naturally used as an pointing organ. However, after some practice, the gap between the two devices narrowed, with the tongue performance only 5% and 57% slower than the finger performance.

These results demonstrate that an isometric tongue pointing device is an effective alternative to hand input devices.

General

Many other forms of the invention exist, each differing from others in matters of detail only.

There can be multiple control elements used and/or located with the mouthpiece. The multiple control elements are responsive to pressure to operate switch elements related with each respective control element thereby to control the operation of the electronic circuit.

Although the invention is described generally in relation to the application of mouth pressure on the second or third control elements, clearly one or both of the second or third control elements 15 and 16 can alternatively operate under pressure from, for instance, the hand. The pressure may be from a finger, or from the palm of the hand, depending on the design of the control element. In different situations, one or more hands or feet may operate the control elements of the pointing device.

Further, instead of operating or pointing an element on a computer, the device may be used to point or steer other electronic responsive devices. These could be tools or equipment for medical or dental needs or other industrial purposes, as well as steering large mechanical devices such as airplanes and helicopters.

The design of the transfer function, namely, the mapping relation between the force applied to the shaft and the speed of the cursor motion, with consideration to human motor and perceptual characteristics, is critical to the performance of an isometric device. Articles that discuss the design of the transfer function are, e.g., R. C. Barrett, E. J. Selker, J. D. Rutledge, and R. S. Olyha, "Negative Inertia: A Dynamic Pointing Function," *Conference Companion of CHI'95:Human Factors in Computing Systems* (1995), pp. 327–321; J. Rutledge, and T. Selker, "Force-to-Motion Functions for Pointing," D. Diaper et. al (ED.), *Proc. of Human-Computer Interaction*—INTERACT'90 (1990), pp. 701–705, which are herein incorporated by reference. Furthermore, the transfer function for the described device can be optimized for the characteristic of the tongue.

One advantage of using the tongue to operate the first control element is the ability to activate the control element in the sense that the tongue can generally surround or envelop the pointing stick of the first control element about a substantial part of its face, and not only the tip of the pointing stick.

Furthermore, different kinds of transducers can be used, for instance, optical transducers. Also, although the first control element is described as being operable with a pointing stick, it is clearly operable with other kinds of activation elements, for instance a resistance/capacitive pad can be formed as part of the mouthpiece or a trackball can be housed with the mouthpiece.

Different forms of electrical connection of the pointing device with the operational element such as a computer can be provided. For instance, as an alternative to the hard wire system, there can be an infrared wireless connection 41 between the device and computer as illustrated in FIG. 5.

An advantage of having an isometric pointing device is that it does not require a substantial operating space. Thus the invention is preferably, but not exclusively, directed to such a device. In some cases the device may be near-isometric, or be relatively self-centering or elastic. For instance, this could be a joystick which is biased to a neutral or self-centering position. In other forms of the invention the stick can be directed at a different angle from the mouthpiece or a different angle to the tongue. The stick may take different shapes, namely it may be more straight, it may be provided with pocket areas to accommodate the tongue or different protrusions which can be engaged differently by the tongue. Accordingly, specific shapes and formats can be provided to the control element and its surface so as to enhance its engagement with the tongue and to provide for sensitive operation.

The invention is to be determined solely in terms of the following claims.

What is claimed is:

1. A tongue-operated pointing device for use with an element to be moved on a computer display comprising:
    (a) an electronic circuit, the circuit including a transducer responsive element; and
    (b) a control element comprising a pressure sensitive isometric portion having a surface for tongue interaction to cause the control element to interact with the transducer responsive element to operate the electronic circuit, the pressure sensitive isometric portion translates pressure and direction of tongue interaction to a corresponding directional movement and velocity of the element.

2. A pointing device as claimed in claim 1, including a mouthpiece for fitting at least partially in the mouth for mounting the control element, and wherein the pressure sensitive isometric portion projects into the cavity above the normal position of repose of the tongue.

3. A pointing device as claimed in claim 1, wherein the electronic circuit provides an output signal, and including means for transmitting the output signal for operating a computer.

4. A tongue operated pointing device for use with an element to be moved on a computer display comprising:
    (a) an electronic circuit including a transducer responsive element;
    (b) a control element comprising a pressure sensitive isometric portion having a surface for application of tongue pressure such that tongue pressure applied to the surface causes the control element to interact with the transducer responsive element, the pressure sensitive isometric portion translates pressure and direction of tongue interaction with the surface to a corresponding directional movement and velocity of the element; and
    (c) the control element and the transducer responsive element are inter-engaging wherein tongue interaction on a selected place and direction on the surface of the pressure sensitive isometric portion acts to change the condition of the transducer responsive element and to move the element in a direction and velocity corresponding to the tongue interaction.

5. A pointing device as claimed in claim 4 including a mouthpiece for fitting at least partially in the mouth for mounting the control element, and wherein the pressure sensitive isometric portion projects into the cavity above the normal position of repose of the tongue.

6. A pointing device as claimed in claim 5 wherein the mouthpiece is at least partially resilient.

7. An isometric tongue-operated pointing device for use with an element to be moved on a computer display comprising:
    (a) an electronic circuit, the circuit including a transducer responsive element;
    (b) a control element to interact with transducer responsive element to operate the electronic circuit and to move an element, the control element comprising a pressure sensitive isometric portion for tongue interaction, the pressure sensitive isometric portion translates pressure and direction of tongue interaction to a corresponding directional movement and velocity of the element; and
    (c) the electronic circuit including means for providing an output signal in response to the condition of the transducer responsive element, and including means for transmitting the output signal to a computer.

8. A pointing device as claimed in claim 7 including a mouthpiece for fitting at least partially in the mouth for mounting the control element, and wherein the pressure sensitive isometric portion projects into the cavity above the normal position of repose of the tongue.

9. A pointing device as claimed in claim 8 wherein the mouthpiece is at least partially resilient.

* * * * *